United States Patent
Andre et al.

(10) Patent No.: US 7,988,982 B2
(45) Date of Patent: Aug. 2, 2011

(54) COSMETIC COMPOSITION WITH ANTI-FREE RADICAL ACTIVITY

(75) Inventors: Patrice Andre, Neuville aux Bois (FR); Isabelle Renimel, Trainou (FR); Céline Godenir, Theillay (FR); Michel Hocquaux, Paris (FR)

(73) Assignee: LVMH Recherche, Paris (FR)

( * ) Notice: Subject to any disclaimer, the term of this patent is extended or adjusted under 35 U.S.C. 154(b) by 583 days.

(21) Appl. No.: 11/883,779

(22) PCT Filed: Jun. 11, 2007

(86) PCT No.: PCT/FR2007/051405
§ 371 (c)(1),
(2), (4) Date: Aug. 6, 2007

(87) PCT Pub. No.: WO2007/144530
PCT Pub. Date: Dec. 21, 2007

(65) Prior Publication Data
US 2009/0142420 A1    Jun. 4, 2009

(30) Foreign Application Priority Data
Jun. 12, 2006 (FR) .................................... 06 52099

(51) Int. Cl.
*A61K 8/02* (2006.01)
(52) U.S. Cl. ....................... 424/401; 514/458
(58) Field of Classification Search .................. None
See application file for complete search history.

(56) References Cited

U.S. PATENT DOCUMENTS

| 6,124,268 | A | 9/2000 | Ghosal |
| 6,756,045 | B1 | 6/2004 | Neudecker et al. |
| 6,914,075 | B2 * | 7/2005 | Nakano et al. ............. 514/547 |
| 2003/0236236 | A1 | 12/2003 | Chen et al. |
| 2004/0197282 | A1 | 10/2004 | Neudecker et al. |
| 2005/0090553 | A1 | 4/2005 | Shapiro |
| 2005/0266064 | A1 | 12/2005 | McCarthy |

FOREIGN PATENT DOCUMENTS
WO    WO 01/87256 A1    11/2001
* cited by examiner

*Primary Examiner* — Susan Hoffman
(74) *Attorney, Agent, or Firm* — Merchant & Gould P.C.

(57) ABSTRACT

A cosmetic composition has an association of at least three of the following substances with anti-free radical activity, selected from:
1) ebselen; or idebenone; or an association of the two; and
2) at least one substance with anti-free radical activity, or at least two substances with anti-free radical activity for obtaining said association of at least three substances with anti-free radical activity, said substance(s) being selected from:
a) a substance of chemical formula (I) below:

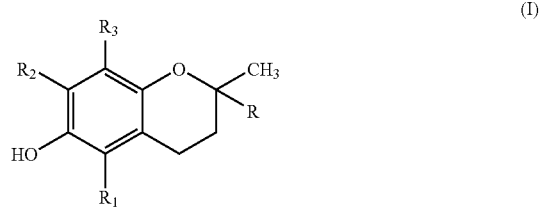

(I)

in which:
R=a linear or branched, saturated or unsaturated $C_1$-$C_{16}$ hydrocarbon chain; and
$R_1$, $R_2$ and $R_3$ are identical or different and are a hydrogen atom or a methyl or methoxy radical,
and its esters;
b) an extract of Edelweiss;
c) an extract of Emblica; and
d) N-acetylcysteine.
The anti-free radical activity is greatly improved.

5 Claims, 2 Drawing Sheets

COSMETIC COMPOSITION WITH ANTI-FREE RADICAL ACTIVITY

The invention relates to a cosmetic composition with anti-free radical activity.

More particularly, the invention provides a cosmetic composition with improved anti-free radical activity comprising an association of at least three substances with anti-free radical activity, the use of such an association as a cosmetic agent or for the manufacture of a composition with improved anti-free radical activity, or a method of cosmetic care in which said composition is applied.

STATE OF THE ART

Document U.S. Pat. No. 6,756,045 B1 discloses a cosmetic composition and a method of cosmetic care comprising idebenone as an anti-free radical agent.

It is well known to those skilled in the art to use, in association with an anti-free radical agent, other antioxidants known for their free radical scavenging properties. Said document also discloses the possibility of adding to the idebenone antioxidants and/or free radical scavengers that are generally known in the literature (column 7, line 20 to column 8, line 14), but without demonstrating any kind of improvement obtained by combining said antioxidants and/or free radical scavengers.

The Examples mention idebenone either on its own or in combination with alpha-tocopherol or beta-carotene, without demonstrating specific effects of this combination in terms of activity towards free radicals.

Reference SHAPIRO US-2005/090,553 relates to a composition and to a method for the treatment of chronic inflammatory diseases by oral route, contrary to the invention which aims to a cosmetic composition applied via topical route.

Reference McCarthy US 2005/266,064 relates to an anti-aging composition comprising notably in EXAMPLE 7 a selenium acceptable form, vitamin E and N-acetyl-cystein, see page 9, paragraph [0134] to [0146]. It is set forth in addition that the selenium appropriate form may be either glutathione peroxidase or selenium under inorganic form. According to the inventor's knowledge, glutathione peroxidase as well as the inorganic form of selenium (selenium ion) do not have any activity of scavenging free radicals, contrary to selenium in the form of Ebselen. It results therefrom that the potential selenium derivatives described in this reference McCarthy are not selected with a view of scavenging free radicals as claimed in the present invention.

TECHNICAL PROBLEMS TO BE SOLVED

One object of the invention is to solve the novel technical problem that consists in finding a novel cosmetic formulation which makes it possible for several active substances with free radical scavenging activity to act in association for the purpose of stopping more effectively the cascade in which free radicals are formed, and thus of preventing and/or better combating the damage they cause, such as degradation of the structural proteins of the skin, resulting in accelerated skin ageing.

Another object of the invention is to solve this novel technical problem by means of a solution which makes it possible for several active substances with improved free radical scavenging activity to act in association, i.e. these substances have a virtually perfect compatibility as regards their free radical scavenging activity.

SUMMARY OF THE INVENTION

The invention solves the above-stated novel technical problems for the first time in a simple, safe and reliable manner that can be used on the industrial and commercial scale.

Thus, according to a first feature, the present invention relates to a composition with improved anti-free radical activity, characterized in that it comprises an association of at least three of the following substances with anti-free radical activity, said association comprising:

1) either ebselen; or idebenone; or an association of the two; and
2) at least one substance with anti-free radical activity or at least two substances with anti-free radical activity for obtaining said association of at least three substances with anti-free radical activity, said substance(s) being selected from the group consisting of:

a) a substance with anti-free radical activity of chemical formula (I) below:

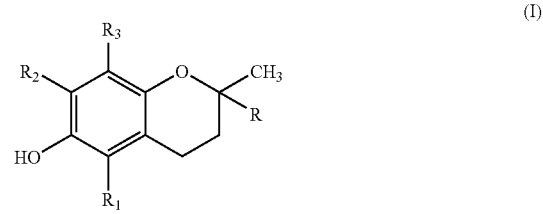

(I)

in which:
R=a linear or branched, saturated or unsaturated $C_1$-$C_{16}$ hydrocarbon chain; and
$R_1$, $R_2$ and $R_3$ are identical or different and are a hydrogen atom or a methyl or methoxy radical,
and its esters with a $C_2$-$C_4$ organic acid, such as acetate, propionate, isopropionate, butyrate or isobutyrate;

b) an extract of Edelweiss;
c) an extract of Emblica; and
d) N-acetylcysteine.

In one advantageous embodiment of the invention, the composition is characterized in that, in chemical formula (I) given above, R=$CH_3$ or a group selected from:

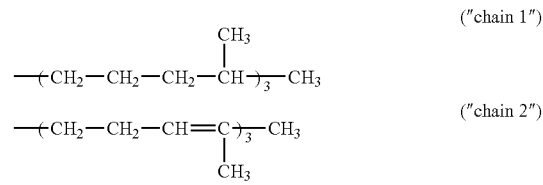

In another advantageous embodiment of the invention, the composition is characterized in that the active substance represented by general chemical formula (I) is selected from alpha-tocopherol, alpha-tocotrienol, dimethylmethoxychromanol and their esters mentioned above.

In another advantageous embodiment of the invention, the composition is characterized in that it also comprises vitamin C or one of its cosmetically acceptable derivatives.

In yet another advantageous embodiment of the invention, the composition is characterized in that it comprises an association of at least the following three substances with anti-free radical activity:
  ebselen;
  idebenone; and
  at least one substance of formula I and/or its esters, preferably alpha-tocotrienol and/or its esters.

In another advantageous embodiment of the invention, the composition is characterized in that it comprises an association of the following three active substances, or comprises an association of the following three substances with anti-free radical activity only as an anti-free radical agent:
  ebselen;
  alpha-tocotrienol and/or its esters; and
  N-acetylcysteine.

In another advantageous embodiment of the invention, the composition is characterized in that it comprises an association of the following three substances, or comprises an association of the following three substances with anti-free radical activity only as an anti-free radical agent:
  ebselen;
  an extract of Emblica; and
  N-acetylcysteine.

In another advantageous embodiment of the invention, the composition is characterized in that it comprises an association of the following three substances, or comprises an association of the following three substances with anti-free radical activity only as an anti-free radical agent:
  ebselen;
  an extract of Edelweiss; and
  N-acetylcysteine.

In another advantageous embodiment of the invention, the composition is characterized in that it comprises an association of the following three active substances, or comprises an association of the following three substances with anti-free radical activity only as an anti-free radical agent:
  ebselen;
  an extract of Edelweiss; and
  idebenone.

In another advantageous embodiment of the invention, the composition is characterized in that it comprises an association of the following three active substances, or comprises an association of the following three substances with anti-free radical activity only as an anti-free radical agent:
  ebselen;
  alpha-tocotrienol and/or its esters; and
  idebenone.

In another advantageous embodiment of the invention, the composition is characterized in that it comprises an association of the following three active substances, or comprises an association of the following three substances with anti-free radical activity only as an anti-free radical agent:
  idebenone;
  alpha-tocotrienol and/or its esters; and
  N-acetylcysteine.

In another advantageous embodiment of the invention, the composition is characterized in that, independently:
  the ebselen is present in a concentration of between 0.02% and 2% by weight;
  the idebenone is present in a concentration of between 0.002% and 0.2% by weight;
  the anti-free radical substance of formula (I) is present in a concentration of between 0.01% and 1% by weight;
  the extract of Edelweiss is present in a concentration of between 0.01% and 1% by weight;
  the extract of Emblica is present in a concentration of between 0.02% and 2% by weight; and
  the N-acetylcysteine is present in a concentration of between 0.02% and 2% by weight.

According to a second feature, the present invention further relates to the use of an association of at least three of the following substances with anti-free radical activity, said association comprising:
  1) either ebselen; or idebenone; or an association of the two; and
  2) at least one substance with anti-free radical activity or at least two substances with anti-free radical activity for obtaining said association of at least three substances with anti-free radical activity, said substance(s) being selected from the group consisting of:
    a) a substance with anti-free radical activity of chemical formula (I) below:

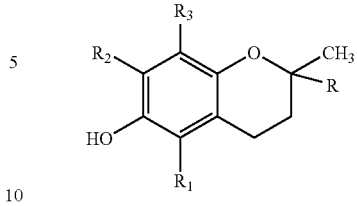

(I)

in which:
R=a linear or branched, saturated or unsaturated $C_1$-$C_{16}$ hydrocarbon chain; and
$R_1$, $R_2$ and $R_3$ are identical or different and are a hydrogen atom or a methyl or methoxy radical,
and its esters with a $C_2$-$C_4$ organic acid, such as acetate, propionate, isopropionate, butyrate or isobutyrate;
    b) an extract of Edelweiss;
    c) an extract of Emblica; and
    d) N-acetylcysteine,
as a cosmetic agent, or for the manufacture of a cosmetic composition with improved anti-free radical activity.

According to a third feature, the present invention further relates to a method of cosmetic care, characterized in that it comprises the determination of at least one zone of the skin, integument or hair of a person in need of care or protection from the action of free radicals, and the topical application, to said zone of the skin, integument or hair, of a cosmetic composition as defined above, or as resulting from the following description referring to the Examples and Figures, in an effective amount for protection from the action of free radicals.

As it will readily be understood by those skilled in the art, in one particular embodiment of the second or third feature, each of these active substances is as defined in the various particular embodiments of the first feature.

Furthermore, the expression "effective amount for protection from the action of free radicals" is understood as meaning the minimum effective amount of the association of at least three aforementioned substances with anti-free radical activity for achieving an effective protective action against free radicals.

Those skilled in the art will readily know how to determine this effective amount, especially on the basis of the illustrative Examples of the invention given below.

Likewise, the expression "topical composition" denotes a composition applied topically to the skin, hair or integument, preferably in the form of a topical cosmetic composition.

Furthermore, one skilled in the art and/or the person wishing to effect care or protection from the action of free radicals is perfectly familiar with the step for determining at least one zone of the skin, integument or hair that is in need thereof. In general, such zones are mainly zones of the skin that are exposed to the sun or actinic radiation—principally the face and the upper and lower limbs—and the hair.

The invention can of course be associated with any other cosmetically acceptable active substance well known to those skilled in the art, can be used for any application in which an anti-free radical action is desired, and can be implemented in a variety of forms, e.g. a cream, a lotion, a make-up foundation, a milk or a gel, or alternatively a stick or a compact powder.

Moreover, those skilled in the art are perfectly familiar with cosmetically acceptable excipients, some of which are mentioned by way of illustration in the Examples of topical compositions given below.

Furthermore, within the framework of the invention, any cosmetic care is effected by topical application to a zone of the skin, integument or hair which is in need of an anti-free radical action, particularly in order to effect an antiwrinkle action on a zone of the skin that exhibits wrinkles.

Other objects, characteristics and advantages of the invention will become clearly apparent to those skilled in the art from the following description referring to various Examples of the invention, which are given simply by way of illustration and cannot therefore in any way limit the scope of the invention.

In the Examples, all the percentages are given by weight, the temperature is room temperature or is given in degrees Celsius and the pressure is atmospheric pressure, unless indicated otherwise.

EXAMPLES ACCORDING TO THE INVENTION

Example 1

Figure 1:
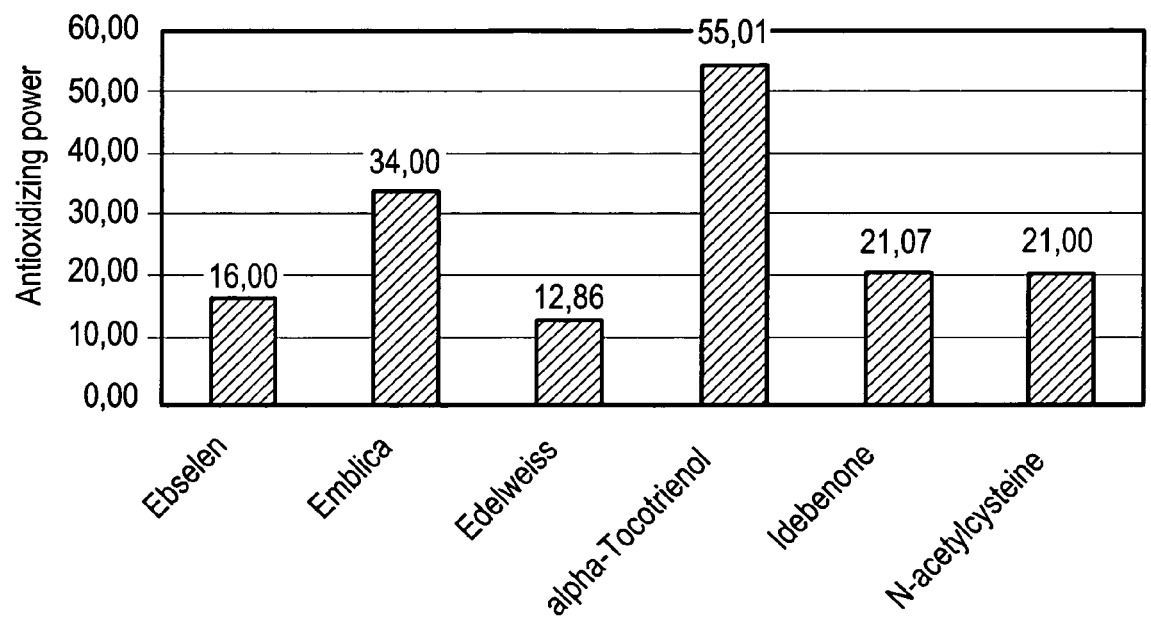
FIG. 1 is a graph showing the antioxidizing power (as defined below), expressed as a percentage, of each of the substances with anti-free radical activity used within the framework of the invention, said antioxidizing power being obtained from the values of the fluorescence signal measured with a fluorescent probe of the type dichlorofluorescein diacetate (DCFH-DA)

Determination of the Antioxidizing Power of Associations of Substances with Anti-Free Radical Activity According to the Invention I) Determination of the Antioxidizing Power of Substances with Anti-Free Radical Activity which can be Used within the Framework of the Invention In a first step the antioxidizing power of substances with anti-free radical activity which can be used within the framework of the invention is determined.

A) Definition of Antioxidizing Power in Terms of the Present Invention

The inventors attempted to quantify the free radical scavenging power of each substance with anti-free radical activity, taken firstly in isolation and then in combination in order to determine the associations that possess an improved free radical scavenging power.

To do this, the inventors used an in vitro test on a model of human keratinocytes, which consisted in the in situ generation of free radicals in the presence and absence of substances with anti-free radical activity, and then in quantification, with the aid of a fluorescent probe of the type dichlorofluorescein diacetate (DCFH-DA), of the free radicals still present in the cells. This probe is well known to those skilled in the art and its use makes it possible to measure the amount of free radicals present as a function of the fluorescence signal emitted.

The antioxidizing power according to the invention, which corresponds in practice to the free radical scavenging power of each substance with anti-free radical activity or an association of such substances, is obtained using the following formula (A):

$$\text{antioxidizing power} = (100 - \Delta \text{test}/\Delta \text{control}) \times 100 \qquad (A)$$

in which:
Δ control=difference in fluorescence values between the control not treated with an active substance or an association of such substances, and the control treated with the reference oxidizing agent hydrogen peroxide ($H_2O_2$);
Δ test=difference in fluorescence values between the control treated with an active substance or an association of active substances, and the control treated with $H_2O_2$.

In practice, the value of Δ control represents the situation where the oxidation is greatest. This value is to be considered as that of 100% oxidation. It is then possible, by taking the ratio (Δ control/Δ test)×100, to determine the percentage oxidation in the presence of an active substance or an association of such active substances. The antioxidizing power can then be calculated as the difference from the maximum value of 100, corresponding to application of the above formula.

The antioxidizing power defined in this way represents the capacity of a substance with anti-free radical activity or an association of such active substances to protect the treated cells from free radicals. Said power can therefore also be interpreted as a percentage protection or protective power.

B) Materials and Method

1) Operating Principle of a DCFH-DA Probe

The use of this probe is well known to those skilled in the art. It is a stable, permeable probe using 2',7'-dichlorodihydrofluorescein diacetate (DCFH-DA), which is widely employed for measuring oxidizing stress in cells.

When the diacetate form of dichlorofluorescein is added to cells, it diffuses across the cell membrane and is then hydrolyzed by intercellular esterases to free DCFH. When the latter compound reacts with an oxidizing species, in particular a free radical, the highly fluorescent compound 2',7'-dichlorofluorescein (DCF) is formed.

The fluorescence emitted is then directly proportional to the concentration of free radicals that has reacted in the medium.

Thus, in the presence of a substance with anti-free radical activity, the DCFH present in the medium encounters fewer free radicals and the value of the fluorescence signal emitted decreases as a consequence.

The operation of the probe can be summarized as follows:

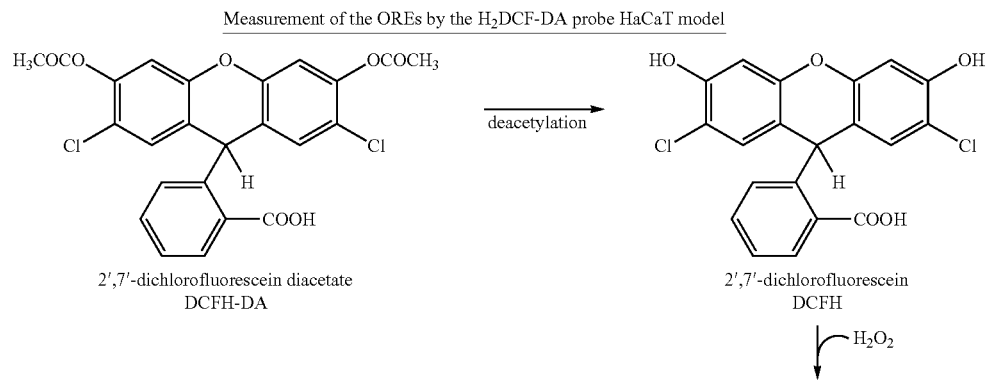

Measurement of the OREs by the $H_2$DCF-DA probe HaCaT model

2',7'-dichlorofluorescein diacetate DCFH-DA

2',7'-dichlorofluorescein DCF

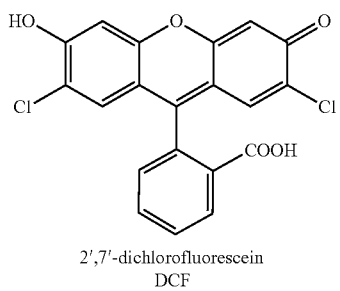
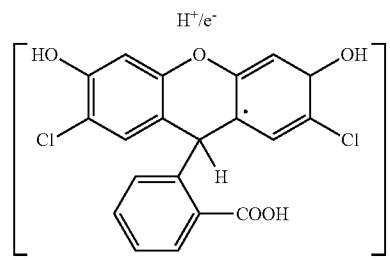

2',7'-dichlorofluorescein
DCF

2) Preparation of the Keratinocytes

Transformed keratinocytes, called HaCaT, are cultivated in keratinocyte serum-free medium (called KSFM$^c$) available from GIBCO under the reference 17005-0034+37000-015. The keratinocytes are inoculated into 96-well micro-plates (at a rate of about 10,000 cells per well).

The first day of culture was noted as D0.

After 24 hours of incubation (D1), the medium is replaced with KSFM$^c$ containing the test molecules at the chosen concentrations, either on their own or in association with at least three substances with anti-free radical activity.

After 24 hours of treatment, the culture medium is discarded and the cells are rinsed with PBS and incubated with 50 µmol of DCFH-DA in complement-free medium at 37° C. for 45 minutes, with agitation.

After the DCFH-DA has been removed, the solutions are washed with PBS and incubated with PBS containing hydrogen peroxide ($H_2O_2$) as a free radical generator.

For each sample, one column of the microplate is not treated with $H_2O_2$ in order to check whether or not the test molecules have excessive oxidizing activity.

The cells loaded with DCFH-DA are placed in a multi-well fluorescence plate reader of the spectra fluor plus type from TECAN, France, at room temperature.

The excitation filter is set to 485 nanometers and the emission filter is set to 535 nanometers.

The fluorescence of each well is measured at T0 and T 20 minutes. It should be noted that a cell viability test is performed after 24 hours of treatment in order to check that the treatments are not toxic to the keratinocytes at the concentrations studied. This is done by the XTT method using a cell proliferation kit II marketed by ROCHE DIAGNOSIS.

3) Chemical Products Used to Operate the DCFH-DA Probe

The 2',7'-dichlorofluorescein diacetate (DCFH-DA) is obtained from MOLECULAR HONEST INC.

The hydrogen peroxide is obtained from SIGMA CHEMICAL COMPANY (Saint Louis, Mo., USA). All the reagents required for the cell culture originate from GIBCO BRL or LIFE TECHNOLOGIES INC.

The substance DCFH-DA is dissolved in dimethyl sulfoxide (DMSO) to form a stock solution, which is kept frozen at −20° C. To load the cells with DCFH, DCFH-DA from the stock solution was mixed with the complement-free medium mentioned above (KSFM$^c$ from GIBCO) to a final concentration of 50 µmol/l.

4) Test Substances with Anti-Free Radical Activity

The ebselen (2-phenyl-1,2-benziselenazol-3(2H)-one) and the N-acetyl-cysteine were obtained from SIGMA CHEMICAL COMPANY (Saint Louis, Mo., USA).

The extract of Emblica, sold under the trade name Emblica™, was obtained from MERCK S. A. in Fontenay-sous-Bois, France. It is an extract of the fruit of Phyllantus emblica, which is in the form of a powder. More generally, an extract of Emblica according to the invention, i.e. an extract rich in polyphenols, can be prepared according to document U.S. Pat. No. 6,124,268.

The extract of Edelweiss is a product from ALPAFLOR (Basel, Switzerland) sold under the trade name Edelweiss GC. An extract of Edelweiss (Leontopodium alpinum) according to the invention, which again is rich in poly-phenols, can be obtained by alcoholic or aqueous-alcoholic extraction, particularly with ethanol, in a proportion ranging from 20 to 100% of alcohol, preferably between 60 and 70% of ethanol. An extract of Edelweiss according to the invention, i.e. an extract rich in polyphenols, especially leontopodic acid, can be prepared according to document WO 0187256.

The extracts of Emblica or Edelweiss are used in the dry form in the tests and Examples described below.

The idebenone (2,3-dimethoxy-6-(10-hydroxydecyl)-5-methyl-1,4-benzo-quinone) was obtained from SPECS in Ryswick, The Netherlands.

The alpha-tocotrienol (hereafter "tocotrienol") was obtained from ORIZA (ISHINOMIYA-CITY, 493-8001 Japan).

C) Results

The results are obtained as the mean of 6 measurement points per sample (N=6) and are plotted on the graph of FIG. 1.

The substances with anti-free radical activity shown here are used in the following concentrations: 0.05 µg/ml for the ebselen, the extract of Emblica and the extract of Edelweiss, and 0.1 µg/ml for the tocotrienol, the idebenone and the N-acetylcysteine.

It can be seen from the individual experiments shown in FIG. 1 that ebselen, extract of Edelweiss, idebenone and N-acetylcysteine are weakly protective substances with anti-free radical activity, whereas tocotrienol and extract of Emblica are substances with a relatively high protective power on the cellular model tested.

II) Determination of the Antioxidizing Power of Associations of Substances with Anti-Free Radical Activity According to the Invention The antioxidizing power of associations of substances with anti-free radical activity according to the invention is determined in a second step.

The method of the first step described above is used to determine the antioxidizing power of different triple associations of the 6 substances with anti-free radical activity tested in the first step.

Figure 2:
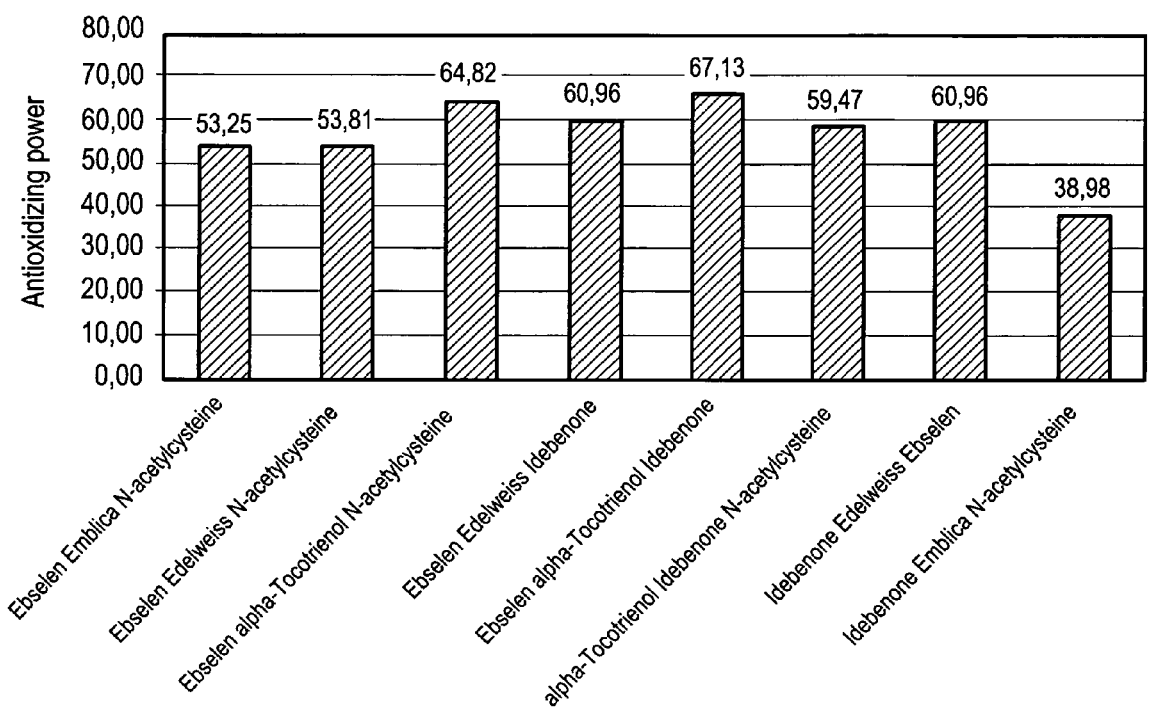
FIG. 2 is a similar graph showing the antioxidizing power of preferred associations of three substances with anti-free radical activity according to the invention.

The results are obtained as the mean of 6 measurement points per sample (N=6) and are plotted on the graph of FIG. 2.

The substances with anti-free radical activity tested in associations are used in the same concentrations as those used in the first step described above in I).

Within the framework of the present invention, the following associations of three substances with anti-free radical activity proved to be particularly effective:
- ebselen, extract of Emblica, N-acetylcysteine,
- ebselen, extract of Edelweiss, N-acetylcysteine,
- ebselen, tocotrienol, N-acetylcysteine,
- ebselen, extract of Edelweiss, idebenone,
- ebselen, tocotrienol, idebenone,
- idebenone, tocotrienol, N-acetylcysteine.

It is seen that the triple associations of the invention show particularly unexpected results compared with the antioxidizing effects obtained for the individual substances and plotted on the graph of FIG. 1.

It is also seen that the comparative double association ebselen/extract of Edelweiss gives poor results, the percentage protection obtained being only 12.1%, whereas the triple association according to the invention, ebselen/extract of Edelweiss/N-acetylcysteine, gives more than 53% and the association idebenone/extract of Edelweiss/ebselen gives more than 60%.

It can therefore be concluded from the above, and by comparing the graph of FIG. 2 with that of FIG. 1, that the associations of at least three substances with anti-free radical activity according to the invention produce unexpected effects that are not obvious to those skilled in the art, in terms of the percentage protection from free radicals.

Examples of Cosmetic Compositions Comprising an Association of Substances with Anti-Free Radical Activity According to the Invention The Examples of topical cosmetic compositions described below are prepared in conventional manner from the following centesimal compositions.

The compositions below are applied to the skin, integument or hair.

Example 2

Anti-Wrinkle Care Cream

| | |
|---|---|
| Glyceryl stearate + PEG-100 stearate | 6.0% |
| Hydrogenated polyisobutene | 3.0% |
| Squalane | 3.0% |
| Glyceryl caprylate/caprate triglycerides | 3.0% |
| Glycerol | 2.0% |
| Octyl methoxycinnamate | 2.0% |
| Cetostearyl octanoate | 1.5% |
| Beeswax | 1.5% |
| Cetyl alcohol | 1.0% |
| Stearyl alcohol | 1.0% |
| Dimethicone | 1.0% |
| Xanthan gum | 0.2% |
| Idebenone | 0.02% |
| Alpha-tocotrienol | 0.1% |
| N-acetylcysteine | 0.2% |
| Preservatives, perfume, colorants | qs |
| Water | qsp |

Example 3

After-Sun Gel

| | |
|---|---|
| Glycerol | 5.0% |
| Caprylic/capric/succinic triglycerides | 5.0% |
| Octyl methoxycinnamate | 1.0% |
| Dimethicone copolyols | 0.5% |
| Acrylates/$C_{10}$-$C_{30}$-alkyl acrylate crosspolymer | 0.5% |
| Ebselen | 0.2% |
| Extract of Emblica (Emblica ™) | 0.2% |
| N-acetylcysteine | 0.2% |
| Preservatives, perfume, colorants | qs |
| Water | qsp |

Example 4

SPF30 Protective Fluid

| | |
|---|---|
| Pentacyclomethicone | 49.0% |
| Titanium dioxide | 15.0% |
| Octyl methoxycinnamate | 7.5% |
| Glycerol | 5.0% |
| Phenyltrimethicone | 5.0% |
| Dimethicone copolyols | 3.0% |
| Polymethyl methacrylate | 2.5% |
| Ebselen | 0.2% |
| Extract of Edelweiss (Edelweiss GC) | 5.0% |
| N-acetylcysteine | 0.2% |
| Preservatives, perfume, colorants, neutralizer | qs |
| Water | qsp |

Example 5

Lip Care Stick

| | |
|---|---|
| Glyceryl caprylate/caprate triglycerides | 20% |
| Castor oil | 12% |
| Hydrogenated isoparaffin | 15% |
| Octyl methoxycinnamate | 8% |
| Candelilla wax | 8% |
| Beeswax | 5% |
| Carnauba wax | 4% |
| Titanium oxides | 2% |
| Talcum | 2% |
| Ebselen | 0.2% |
| Alpha-tocotrienol | 0.1% |
| N-acetylcysteine | 0.2% |
| Preservatives, perfume, colorants, neutralizer | qsp |

Example 6

Body Emulsion

| | |
|---|---|
| Octyl palmitate | 7.0% |
| Glyceryl caprylate/caprate triglycerides | 3.0% |
| Octyl octanoate | 2.0% |
| Phenyltrimethicone | 2.0% |
| Glycerol | 2.0% |
| Stearic acid | 1.0% |
| Sorbitan stearate | 0.9% |

-continued

| | |
|---|---|
| Cetyl alcohol | 0.5% |
| Stearyl alcohol | 0.5% |
| Sorbitan stearate | 0.1% |
| Ebselen | 0.2% |
| Extract of Edelweiss (Edelweiss GC) | 0.1% |
| Idebenone | 0.02% |
| Preservatives, perfume, colorants, neutralizer | qs |
| Water | qsp |

Example 7

Anhydrous Make-Up Foundation

| | |
|---|---|
| Mica | 31.0% |
| Titanium dioxide | 22.4% |
| Talcum | 11.0% |
| Anhydrous silica | 6.0% |
| Nylon-12 | 8.0% |
| Octyl methoxycinnamate | 7.0% |
| Methylphenylpolysiloxane | 2.5% |
| Stearic acid | 2.0% |
| Magnesium stearate | 1.5% |
| Colorants (iron oxides) | 2.5% |
| Phenyltrimethicone | 2.0% |
| Glycerol | 2.0% |
| Idebenone | 0.2% |
| Alpha-tocotrienol | 0.1% |
| N-acetylcysteine | 0.2% |
| Preservatives, perfume, colorants, neutralizer | qsp |

The invention claimed is:

1. A cosmetic composition comprising an association of ebselen; idebenone; and at least one substance with anti-free radical activity of chemical formula (I) below:

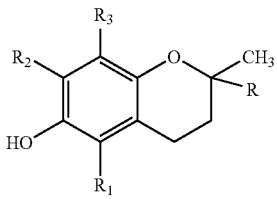

in which:
R is a linear or branched, saturated or unsaturated $C_1$-$C_{16}$ hydrocarbon chain; and
$R_1$, $R_2$ and $R_3$ are identical or different and are selected from a hydrogen atom, a methyl and a methoxy, or an ester of formula I with a $C_2$-$C_4$ organic acid,
wherein
ebselen present in a concentration ranging between 0.02% and 2% by weight;
idebenone present in a concentration ranging between 0.002% and 0.2% by weight; and
the substance of formula (I) present in a concentration ranging between 0.01% and 1% by weight;
wherein the substance represented by general chemical formula (I) is alpha-tocotrienol or an alpha-tocotrienol ester.

2. The cosmetic composition of claim 1, wherein said composition further comprises vitamin C or a cosmetically acceptable compound thereof.

3. A method of cosmetic care, comprising
determining at least one zone of the skin, integument or hair of a person in need of care or protection from the action of free radicals, and
topically applying to said zone of the skin, integument or hair, the cosmetic composition of claim 1 in an effective amount for delaying or combating the damage caused by the action of free radicals.

4. The method of cosmetic care of claim 3, wherein the cosmetic care includes anti-wrinkle care.

5. The method of claim 3, wherein said composition further comprises vitamin C or a cosmetically acceptable compound thereof.

* * * * *